(12) United States Patent
Cedeon

(10) Patent No.: US 6,436,347 B1
(45) Date of Patent: Aug. 20, 2002

(54) INDICATOR DEVICE

(75) Inventor: Andras Cedeon, Stockholm (SE)

(73) Assignee: Mincor AB, Lidingo (SE)

( * ) Notice: Subject to any disclaimer, the term of this patent is extended or adjusted under 35 U.S.C. 154(b) by 0 days.

(21) Appl. No.: 09/580,438

(22) Filed: May 30, 2000

Related U.S. Application Data

(63) Continuation of application No. PCT/SE00/00114, filed on Jan. 20, 2000.

(30) Foreign Application Priority Data

Jan. 21, 1999 (SE) ................................................ 9900180

(51) Int. Cl.$^7$ ............................................. G01N 22/00
(52) U.S. Cl. ............................. 422/56; 422/55; 422/57; 436/127; 436/133; 128/205.23
(58) Field of Search ............... 422/55, 57, 56; 436/127, 133; 128/205.23

(56) References Cited

U.S. PATENT DOCUMENTS

| | | | |
|---|---|---|---|
| 5,005,572 A | * 4/1991 | Raemer et al. | 128/207.14 |
| 5,472,668 A | 12/1995 | Mills et al. | 422/56 |
| 5,480,611 A | * 1/1996 | Mills et al. | 422/55 |

FOREIGN PATENT DOCUMENTS

| | | | |
|---|---|---|---|
| WO | WO 96/24054 | * | 8/1996 |
| WO | WO-0002844 A1 | * | 1/2000 |

OTHER PUBLICATIONS

STN International, File CAPLUS, CAPLUS accession No. 1996:118319, Mills, Andrew et al.: "Measurement of dissolved carbon dioxide using colorimetric polymer films"; Proc. SPIE–Int. Soc. Opt. Eng. (1995). Volume Date 1995, 2631, 100–9.

* cited by examiner

*Primary Examiner*—Jill Warden
*Assistant Examiner*—LaToya Cross
(74) *Attorney, Agent, or Firm*—Browdy and Neimark

(57) ABSTRACT

A fast-response colorimetric carbon dioxide indicator device which is substantially insensitive to humidity and comprises a chemically inert substrate and an indicator composition supported by the substrate and responsive to exposure to carbon dioxide in expired respiratory air to undergo a color changing reaction. The indicator composition includes a pH sensitive dye and a basic substance having the general formula

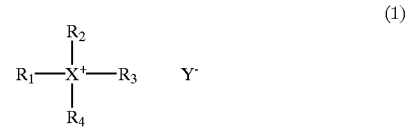

(1)

in which

X is a nitrogen or phosphorus atom, each of $R_1$, $R_2$, $R_3$ and $R_4$ is an alkyl, $Y^-$ is an anion selected from the group consisting of hydroxide, fluoride, chloride, bromide, iodide, carbonate, and tetrafluoroborate, at least one of the alkyls $R_1$, $R_2$, $R_3$ and $R_4$ having at least 13 carbon atoms and at least one of the other alkyls having from 6 to 8 carbon atoms, the remaining alkyls, if any, having from 1 to 12 carbon atoms.

4 Claims, 2 Drawing Sheets

INDICATOR DEVICE

CROSS REFERENCE TO RELATED APPLICATION

The present application is continuation of International Application No. PCT/SE00/00114, filed Jan. 20, 2000, the entire contents of which being hereby incorporated herein by reference.

FIELD OF THE INVENTION

This invention relates to a carbon dioxide indicator device and more particularly to a carbon dioxide indicator device of the kind which comprises a chemically inert substrate and an indicator composition supported by the substrate and responsive to exposure to carbon dioxide in expired respiratory air to undergo a colour changing reaction, said indicator composition including a pH sensitive dye and a basic substance selected from the group consisting of quaternary ammonium and phosphonium salts.

BACKGROUND OF THE INVENTION

Colorimetric carbon dioxide indicator devices of this kind are used to detect the presence of a certain minimum content of carbon dioxide in the air expired by a human being. When the indicator devices are used, the carbon dioxide reacts with the indicator composition to change the pH of the environment in which the pH sensitive dye operates and thereby cause a colour change in the indicator composition.

For example, they can be used to verify that a patient has been correctly intubated, that is, that a tracheal tube has been properly placed in the trachea instead of in the oesophagus. If the tracheal tube has been properly placed, the air expired by the patient through the tracheal tube contains carbon dioxide in an amount that is significantly higher than that of air in the oesophagus; the air in the trachea normally contains 5–6 percent carbon dioxide, whereas the air in the oesophagus normally only contains about 0.03 percent carbon dioxide. A calorimetric carbon dioxide indicator device of the kind mentioned above may be placed inside a transparent portion of the tracheal tube proper or some other device passing the expired air such that the expired air contacts the indicator composition and causes it to change colour, thereby providing a visual indication of the presence of carbon dioxide in the expired air.

In the above-mentioned use, as well as in some other uses, a qualitative detection of carbon dioxide is adequate, so that it suffices that the indicator composition undergoes sufficiently distinct reversible changes of colour rapidly enough to enable an anesthesiologist, for example, to observe the fluctuations of the carbon dioxide content that occur during the inspirations and expirations of the patient. See, for example, U.S. Pat. No. 5,005,572 (Raemer et al), which teaches use of, among other substances, quaternary ammonium or phosphonium salts as part of the indicator composition. These quaternary ammonium and phosphonium salts have the following general formula

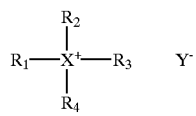

in which
X is a nitrogen or phosphorus atom,
each of $R_1$, $R_2$, $R_3$ and $R_4$ is an alkyl,
$Y^-$ is an anion selected from the group consisting of hydroxide, fluoride, chloride, bromide, iodide, carbonate, and tetrafluoroborate.

More specifically, in these prior art indicator compositions each of the alkyls $R_1$, $R_2$, $R_3$ and $R_4$ have from 1 to 12 carbon atoms.

A recently disclosed compact and inexpensive colorimetric carbon dioxide analyzer suitable for quantitative applications in which, for cost or other reasons, IR-analyzers are unsuited, makes use of a carbon dioxide indicator device of the kind mentioned above, see Anesthesiology, Volume 85, No. 3, Abstract 440 (September 1996).

However, the usefulness of this analyzer is limited by problems inherent in the properties of the carbon dioxide indicator devices now available, notably the response time of the indicator compositions. The time it takes for the indicator composition to undergo a more or less complete change in its colour in response to a sudden exposure to carbon dioxide should be shorter than the duration of the expiration phase of a single breath, i.e. shorter than about half the duration of a single breath. It is desirable for the indicator composition to respond sufficiently rapidly to enable photoelectric calorimetric monitoring of the carbon dioxide variation throughout the expiration phase with an accuracy that is comparable to that which can be achieved with an IR analyzer.

A healthy adult typically breathes at a rate of about 15 breaths per minute at rest so that the duration TE of the expiration phase then is about 2 seconds, a variation of TE within the range of 1.5 to 4 seconds being normal. For children and neonates, the corresponding range is 0.75 to 1.5 seconds and 0.5 to 1 second, respectively.

The response time of prior art carbon dioxide indicator compositions of the kind indicated above is greatly dependent on the humidity of the environment in which the indicator composition operates. Unfortunately, the expired air is saturated with water while the inspired air may be relatively dry. In order that the carbon dioxide indicator composition may provide consistent quantitative indications even when the duration of the expiratory phase is short, say 2 seconds or less, it should therefore be substantially insensitive to the humidity of the environment in which it operates.

It has been proposed to provide for a fast response by incorporating a plasticiser in the carbon dioxide indicator compositions, see U.S. Pat. No. 5,472,668 (Mills et al). However, the incorporation of a plasticiser reduces the shelf life of the indicator devices to a few months, thereby making the indicator devices unsuited for use in commercial instruments.

Replacing plasticisers with other water insoluble substances may resolve the shelf life problem (see WO96/24054) but will not shorten the response time sufficiently to permit an accurate quantitative monitoring of the carbon dioxide variations during the individual expiration phases.

SUMMARY OF THE INVENTION

An object of the present invention is to provide a fast-response calorimetric carbon dioxide indicator device of the kind mentioned initially which is substantially insensitive to humidity variations within the range encountered in its use for indicating carbon dioxide in expired air and the shelf life of which is sufficiently long to enable it to be used in commercial carbon dioxide analyzers.

In the pursuit of such a calorimetric indicator device it has surprisingly been found that indicator compositions, the basic substance of which corresponds to the following general formula (1) and in which at least one of the alkyls $R_1$, $R_2$, $R_3$ and $R_4$ has at least 13 carbon atoms and at least one of the other alkyls has from 6 to 8 carbon atoms, the remaining alkyls, if any, having from 1 to 12 carbon atoms, perform very well in respect of the above-mentioned requirements.

In accordance with this finding, the above-stated object of the invention is achieved with a fast-response calorimetric carbon dioxide indicator device which is substantially insensitive to humidity and comprises a chemically inert substrate and an indicator composition supported by the substrate and responsive to exposure to carbon dioxide in expired respiratory air to undergo a colour changing reaction, said indicator composition including a pH sensitive dye and a basic substance having the general formula

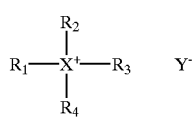

(1)

in which

X is a nitrogen or phosphorus atom, each of $R_1$, $R_2$, $R_3$ and $R_4$ is an alkyl, $Y^-$ is an anion selected from the group consisting of hydroxide) fluoride, chloride, bromide, iodide, carbonate, and tetrafluoroborate, at least one of the alkyls $R_1$, $R_2$, $R_3$ and $R_4$ having at least 13 carbon atoms and at least one of the other alkyls having from 6 to 8 carbon atoms, the remaining alkyls, if any, having from 1 to 12 carbon atoms.

If only one of the alkyls has more than 12 carbon atoms and only one has from 6 to 8 carbon atoms, the other two alkyls are similar or dissimilar to the numbers of carbon atoms being within the range from 1 to 12.

The term alkyl as used in this description and in the claims encompasses both linear and branched alkyls.

In a preferred embodiment of the indicator device according to the invention, $R_1$ is tetradecyl and thus has 14 carbon atoms and each of $R_2$, $R_3$ and $R_4$ is hexyl and thus has 6 carbon atoms.

As in the prior art carbon dioxide indicator, the indicator composition may be provided as a coating on a suitable backing, such as a polymeric sheet, preferably transparent so that the coating can be viewed through it. The coating may also be covered by a protective gas-permeable membrane of a suitable material allowing gaseous carbon dioxide to pass freely through it but blocking passage of liquids.

The dye forming part of the indicator composition may be any of the many different dyes which are conventional in colorimetric carbon dioxide indicators of the kind with which the invention is concerned, such as thymol blue.

For a proper understanding of the present invention it is important to note that the shorter the carbon chains of the alkyls of the basic substance included in the indicator composition according to the invention, the more hydrophilic and water soluble the basic substance. If the carbon chains have more than about 8 carbon atoms, the basic substance is substantially water insoluble and hydrophobic.

However, a certain amount of molecular water has to be present in the indicator composition, because the colour changing reaction requires the carbon dioxide to combine with molecular water. If all four carbon chains contain more than 10–12 carbon atoms, the amount of water present will be insufficient for the colour changing reaction to take place properly, even when the air contacting the indicator composition is humid. If the air is dry, even indicator compositions in which the carbon chains are shorter fail to respond properly to exposure to carbon dioxide. For example, when all carbon chains have 8 atoms and a hydrophilic substance is not incorporated in the indicator device, no reliable quantitative indication of carbon dioxide is possible if the gas containing the carbon dioxide has a relative humidity below about 20% (A Gedeon, P Krill and C Mebius, Anesthesia 49, 798–103, 1994).

If, on the other hand, the indicator composition is too hydrophilic, because the number of carbon atoms of the carbon chains is much smaller than 8 and/or because the indicator composition includes a strongly hydrophilic substance, the indicator composition will respond very slowly to carbon dioxide. Particularly in the humid environment in which the indicator device operates in clinical use, the response will be useless for accurate capnographic recording, as will be shown below.

BRIEF DESCRIPTION OF THE DRAWINGS

The lengths of the carbon chains of the indicator composition therefore should be matched such that a suitable balance between the hydrophobic properties of the chain or chains having at least 13 carbon atoms and the hydrophilic properties of the shorter carbon chain or chains is achieved. For example, as will become apparent as the description proceeds, an indicator composition in which one of the carbon chains has 14 carbon atoms and the other three carbon chains each have 6 carbon atoms confers excellent carbon dioxide response properties on the indicator device according to the invention.

The invention will be further elucidated below with reference to the accompanying drawings, in which.

DETAILED DESCRIPTION OF THE INVENTION

Figure 1:
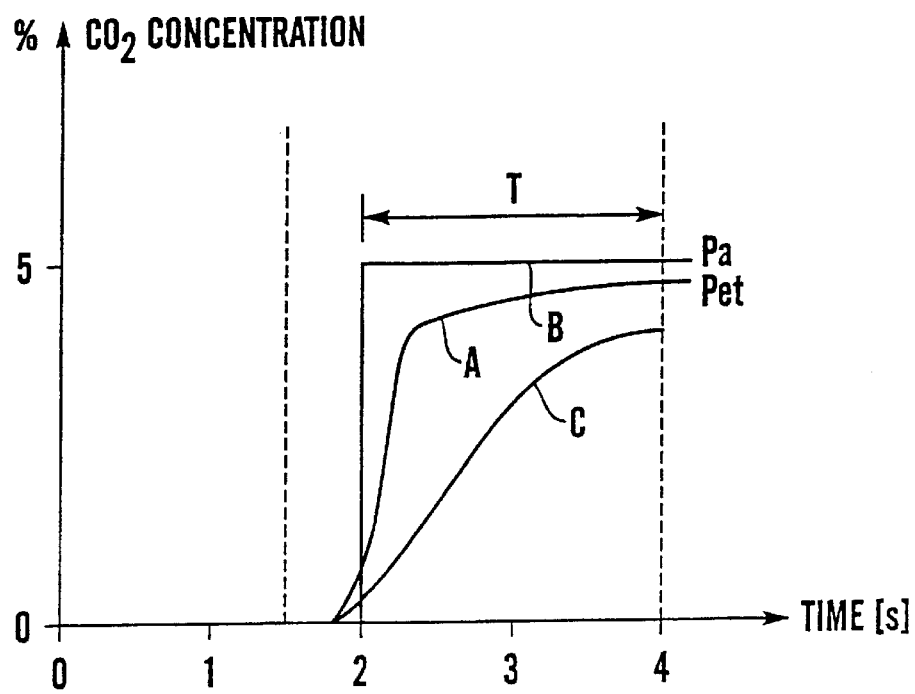
FIG. 1 is a diagram illustrating the variation of the carbon dioxide concentration of respiratory air over time during the expiration phase of a breath.

In the respiratory process of human beings the lungs take up oxygen from the pulmonary blood and give up carbon dioxide to the air. Normally, almost no carbon dioxide is present in the inspired air, whereas the expired air contains a substantial amount of carbon dioxide. A curve, the so-called capnogram, representing the variation over time of the carbon dioxide content of the air present in the upper airways during the expiratory phase of a breath generally has the shape illustrated by the graph A in FIG. 1. This graph represents the normal breathing of a healthy adult person; the breathing rate is 15 breaths per minute, so that each breath takes four seconds, the durations T of the inspiratory and expiratory phases being roughly equal, that is, about 2 seconds. The carbon dioxide partial pressure Pet at the end of the expiratory phase corresponds to a carbon dioxide concentration of roughly 5%.

The shape of the capnogram for an idealised, completely homogenous lung is as illustrated by curve B, showing that the carbon dioxide partial pressure Pa in the alveoles rises almost instantaneously and then remains constant for the duration of the expiratory phase. A significant deviation from the shape represented by curve B, e.g. as is illustrated by curve C, indicates that the gas exchange process in the lungs is inefficient and, accordingly, indicates a disease, the severity of which can be assessed from the capnogram.

Moreover, for a healthy person the end-expiratory carbon dioxide concentration should be close to the carbon dioxide concentration in the lungs, and the difference between $P_a$ and $P_{et}$ indicates whether the inspired and expired gas volumes and the blood flow through the lungs are adequate.

There is therefore a need for a simple and reliable technique for accurately sensing the variation of the carbon dioxide concentration of the expired air. The calorimetric indicator device according to the present invention enables this need to be met.

Figure 2:
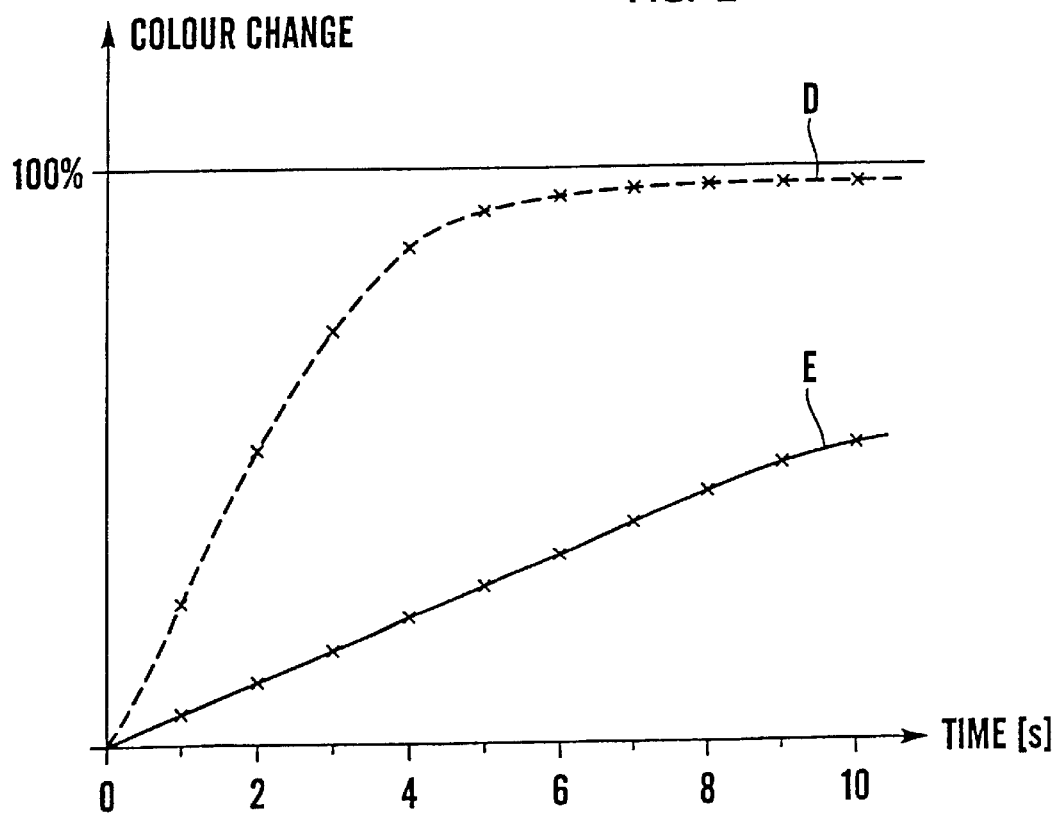
FIG. 2 is a diagram showing colour change as sensed by a strongly hydrophilic prior art carbon dioxide indicator during the expiration phase of a breath.

FIG. 2 shows capnograms recorded by means of the calorimetric carbon dioxide analyzer mentioned above, using an indicator device including an indicator composition in which the basic substance has the general formula (1) and in which the four alkyls $R_1$, $R_2$, $R_3$, and $R_4$ are similar and each has one carbon atom, i.e. each is methyl. The broken-line capnogram D represents substantially dry air while the broken-line capnogram E represents respiratory air of normal humidity. The colour change over time is plotted against the ordinate or Y-axis, and the horizontal line above the last-mentioned capnogram indicates the 100% or completed colour changing reaction.

As is evident from FIG. 2, the humidity of the gas significantly affects the colour change and it is apparent that this prior art indicator device is virtually useless for quantitative measurements.

Figure 3:
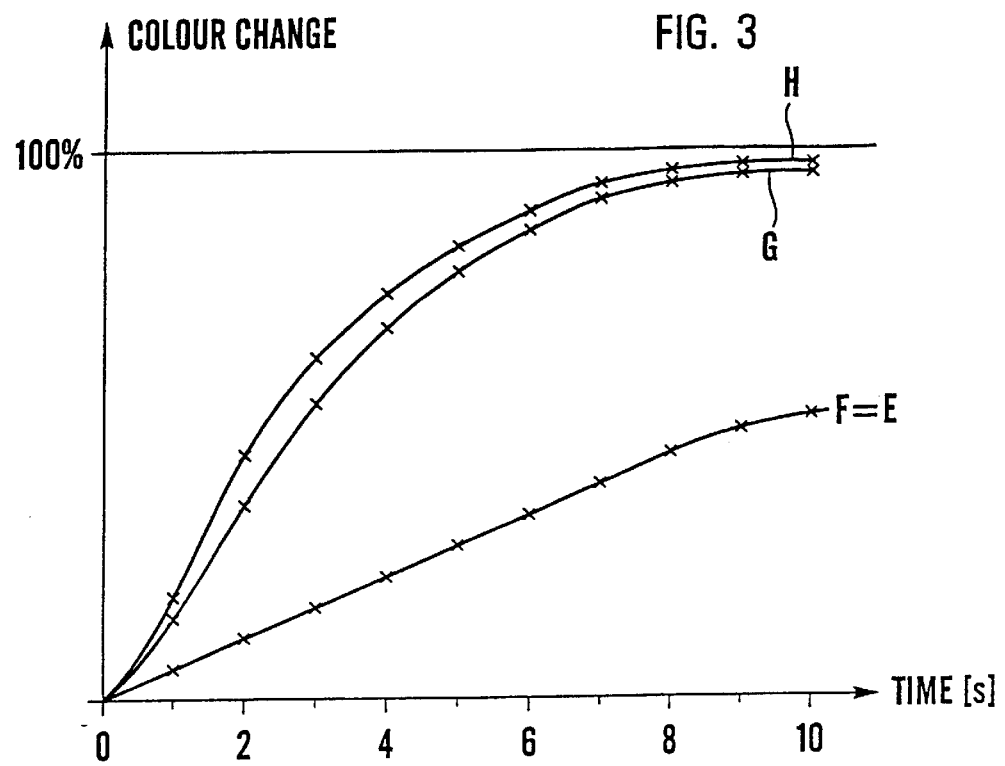
FIG. 3 is a diagram similar to FIG. 2 and shows colour change as sensed by a different prior art carbon dioxide indicator device and by a carbon dioxide indicator device having a modified reaction enhancing substance, the diagram also including the solid-line graph of FIG. 2 to facilitate comparison of the graphs.

In FIG. 3, capnogram F is the same as capnogram E of FIG. 2. Capnograms G and H also represent indicators in which the basic substance of the indicator composition has the general formula (1). Moreover, all three capnograms have been recorded for humid air.

In the indicator represented by capnogram G, the alkyl $R_1$ had 16 carbon atoms (i.e. was hexadecyl) while the alkyls $R_2$, $R_3$, and $R_4$ each had one carbon atom (i.e. was methyl). The response of the carbon dioxide indicator was significantly faster than that of the indicator represented by capnogram F (E) but not fast enough to be satisfactory. In the indicator represented by capnogram H, all four alkyls $R_1$, $R_2$, $R_3$ and $R_4$ each had 8 carbon atoms (tetraoctylammonium hydroxide). The dye used was thymol blue and a water insoluble alcohol was used as a chemical stabilizer. This indicator was also used in the investigation reported in Anesthesiology, Volume 85, No. 3, Abstract 440 (September 1996), cited above. Capnogram H shows a response that is only slightly faster than that shown by capnogram G. Accordingly, this response is also too slow to be satisfactory.

Figure 4:
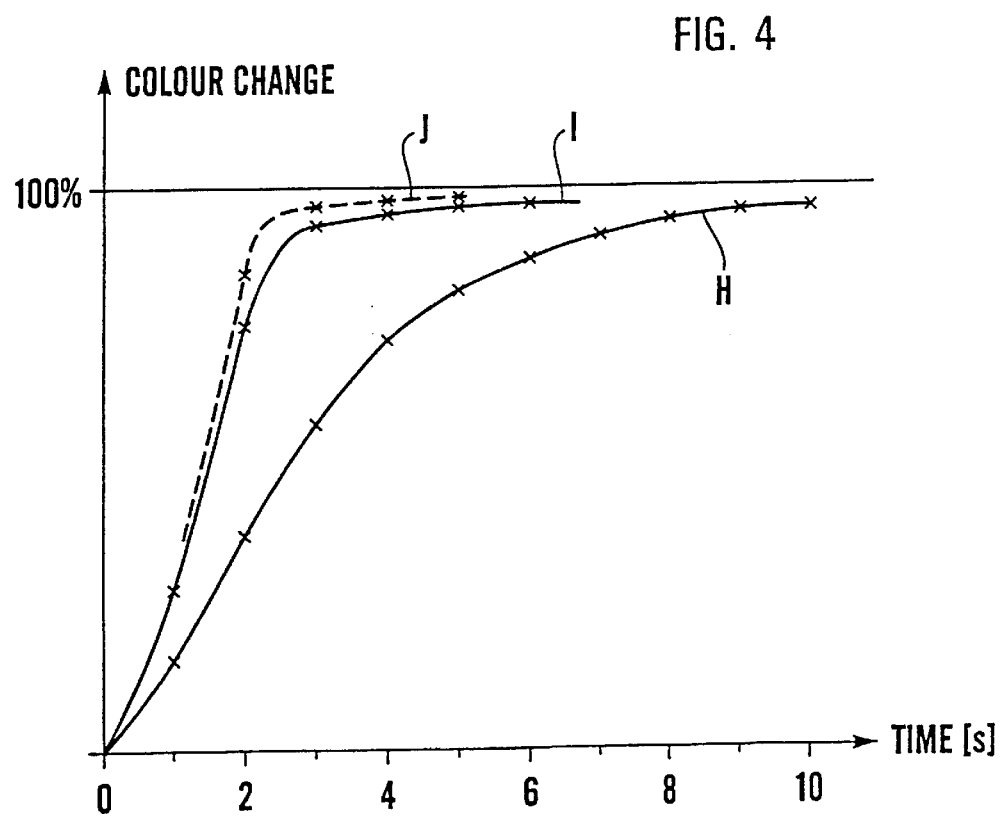
FIG. 4 is a diagram similar to FIGS. 2 and 3 and showing colour change as sensed by a preferred embodiment of the carbon dioxide indicator device according to the invention, the diagram also including for comparison one of the graphs shown in FIG. 3.

FIG. 4 shows capnograms I (solid line) and J (broken line) recorded with an indicator device according to a presently preferred embodiment of the invention, namely an indicator device including in the indicator composition a basic substance having the general formula (1) with the alkyl $R_1$ having 14 carbon atoms and the other alkyls $R_2$, $R_3$ and $R_4$ each having 6 carbon atoms (i.e. hexyl); the substance thus was tetradecyltrihexylammonium hydroxide. This indicator otherwise was free from materials affecting the balance between the hydrophilic and hydrophobic properties conferred on the indicator by the lengths of the carbon chains or affecting the permeability to carbon dioxide of the indicator. Capnogram I was recorded for humid air and capnogram J was recorded for dry air. FIG. 4 also includes a capnogram H which is the same as capnogram H in FIG. 3.

As is evident from FIG. 4, the indicator device according to the invention as represented by capnograms I and J has excellent response properties both under dry and wet conditions in that the time required for the colour change reaction to be substantially (90%) completed is about two seconds. This represents a drastic improvement in comparison with the best prior art indicator device.

The above examples show that in order to achieve a fast response and at the same time the properly balanced hydrophilic character necessary to produce the pH change required for the colour changing process to take place in response to exposure to carbon dioxide, one can use in the indicator composition a basic substance having the general formula (1) in which at least one of the alkyls has more than 12 carbon atoms, while at least one of the other alkyls is shorter and preferably has from 6 to 8 carbon atoms. In this way, the basic substance forming part of the indicator composition can be tailored so as to provide an indicator device having the required fast response under all normal clinical conditions without any additional chemical substance being required in the indicator composition.

The indicator according to the invention can take any suitable physical shape, e.g. as shown in U.S. Pat. No. 4,728,499 (Fehder), U.S. Pat. No. 4,879,999 (Leiman et al), U.S. Pat. No. 5,005,572 (Raemer) and 5,472,668 (Mills et al). Accordingly, the indicator composition may be absorbed into a porous substrate sheet of polypropylene or applied as a coating to a non-porous substrate sheet. If desired, the indicator may also comprise a rigid or flexible backing and a protective cover sheet applied over the indicator composition.

What is claimed is:

1. A fast-response calorimetric carbon dioxide indicator device which is substantially insensitive to humidity and comprises a chemically inert substrate and an indicator composition supported by the substrate and responsive to exposure to carbon dioxide in expired respiratory air to undergo a colour changing reaction, said indicator composition including pH sensitive dye and a basic substance having the general formula

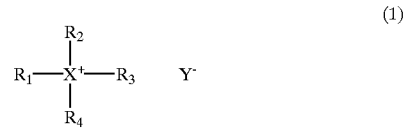

(1)

in which
X is nitrogen or phosphorus atom,
each of $R_1$, $R_2$, $R_3$, and $R_4$ is an alkyl,
$Y^-$ is an anion selected from the group consisting of hydroxide, fluoride, chloride, bromide, iodide, carbonate, and tetrafluoroborate,
at least one of the alkyls $R_1$, $R_2$, $R_3$ and $R_4$ having at least 13 carbon atoms and at least one of the other alkyls having from 6 to 8 carbon atoms, the remaining alkyls, if any, having from 1 to 12 carbon atoms; the remaining alkyls, if any, is any alkyl in the formula that does not have at least 13 carbon atoms or 6–8 carbon atoms.

2. A fast-response calorimetric carbon dioxide indicator device as claimed in claim 1, in which only one of the alkyls has 14 carbon atoms and each of the other three alkyls has 6 carbon atoms.

3. A fast-response calorimetric carbon dioxide indicator device as claimed in claim 1, in which the indicator composition includes no additional substance affecting the hydrophilic properties of the indicator composition or the permeability thereof to carbon dioxide.

4. A fast-response calorimetric carbon dioxide indicator device as claimed in claim 1, in which the indicator composition is applied as a coating to the substrate.

\* \* \* \* \*

UNITED STATES PATENT AND TRADEMARK OFFICE
CERTIFICATE OF CORRECTION

PATENT NO.    : 6,436,347 B1
DATED         : August 20, 2002
INVENTOR(S)   : Andres Gedeon It is certified that error appears in the above-identified patent and that said Letters Patent is hereby corrected as shown below:

<u>Title page,</u>
Item [12] and Item [75], delete "Cedeon" and insert therefor -- Gedeon --;

<u>Column 1,</u>
Line 39, delete "calorimetric" and insert therefor -- colorimetric --;

<u>Column 2,</u>
Lines 33 and 59, delete "calorimetric" and insert therefor -- colorimetric --;

<u>Column 3,</u>
Line 8, delete "calorimetric" and insert therefor -- colorimetric --;

<u>Column 5,</u>
Lines 23 and 27, delete "calorimetric" and insert therefor -- colorimetric --;

<u>Column 6,</u>
Line 43, delete "calorimetric" and insert therefor -- colorimetric --;

<u>Column 7,</u>
Lines 4 and 8, delete "calorimetric" and insert therefor -- colorimetric --;

<u>Column 8,</u>
Line 4, delete "calorimetric" and insert therefor -- colorimetric --.

Signed and Sealed this

Fourteenth Day of January, 2003

JAMES E. ROGAN
*Director of the United States Patent and Trademark Office*